United States Patent [19]
Poetsch et al.

[11] Patent Number: 5,384,072
[45] Date of Patent: Jan. 24, 1995

[54] METHYLENECYCLOBUTANE DERIVATIVES

[75] Inventors: Eike Poetsch, Mühltal; Werner Binder, Dieburg; Thomas Geelhaar, Mainz, all of Germany

[73] Assignee: Merck Patent Gesellschaft mit Beschrankter Haftung, Darmstadt, Germany

[21] Appl. No.: 119,071

[22] PCT Filed: Mar. 4, 1992

[86] PCT No.: PCT/EP92/00478
§ 371 Date: Sep. 15, 1993
§ 102(e) Date: Sep. 15, 1993

[87] PCT Pub. No.: WO92/16483
PCT Pub. Date: Oct. 1, 1992

[30] Foreign Application Priority Data

Mar. 16, 1991 [DE] Germany .............................. 4108713

[51] Int. Cl.$^6$ ...................... C09K 19/30; C07C 69/74; G02F 1/13
[52] U.S. Cl. .............. 252/299.63; 252/299.01; 359/103; 560/123
[58] Field of Search ...................... 252/299.63, 299.01; 359/103; 560/123

[56] References Cited

FOREIGN PATENT DOCUMENTS 0330216 8/1989 European Pat. Off. .

OTHER PUBLICATIONS

Dolbier, "The effect of styrene alpha–substituents on the regiochemistry of (2+2) cycloadditions with difluoroallene", *Tetrahedron Letters*, vol. 28, No. 14 (1987), pp. 1491–1492.

*Primary Examiner*—Shean Wu
*Attorney, Agent, or Firm*—Millen, White, Zelano & Branigan

[57] ABSTRACT

The invention relates to methylenecyclobutane derivatives of the formula I

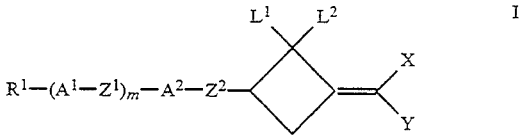

in which $R^1$, $A^1$, $A^2$, $Z^1$, $Z^2$, $L^1$, $L^2$, X, Y and m are as defined in claim 1, and to the use thereof as a component of liquid-crystalline media for electrooptical displays.

13 Claims, No Drawings

METHYLENECYCLOBUTANE DERIVATIVES

SUMMARY OF THE INVENTION

The invention relates to methylenecyclobutane derivatives of the formula I

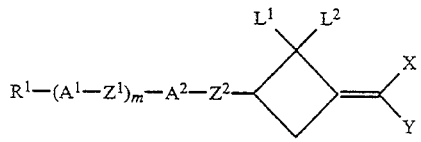

in which

R$^1$ is halogen, CN, CF$_3$, —OCF$_3$, —OCF$_2$H or an alkyl or alkenyl or perfluoroalkyl radical having up to 15 carbon atoms which is unsubstituted or monosubstituted by CN, halogen or CF$_3$, where one or more CH$_2$ groups in these radicals may each, independently of one another, be replaced by —S—,

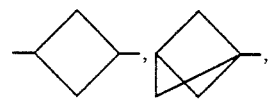

—O—, —CO—, —CO—O—, —O—CO— or —O—CO—O— in such a way that S and/or O atoms are not linked directly to one another, A$^1$ and A$^2$ are each, independently of one another, a
  (a) trans-1,4-cyclohexylene radical in which, in addition, one or more non-adjacent CH$_2$ groups may be replaced by —O— and/or —S—,
  (b) 1,4-phenylene radical in which, in addition, one or two CH groups may be replaced by N,
  (c) radical from the group consisting of 1,3-cyclobutylene, 1,3-bicyclo(1,1,1)-pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) may be monosubstituted or polysubstituted by CN or halogen, L$^1$ and L$^2$ are each H, F or Cl, Z$^1$ and Z$^2$ are each, independently of one another —CH$_2$CH$_2$—, —C≡C—, —CH$_2$O—, —OCH$_2$, —CO—O—, —O—CO—, —CH=N—, —N=CH—, —CH$_2$S—, —SCH$_2$—, a single bond or an alkylene group having 3 to 6 carbon atoms in which, in addition, one CH$_2$ group may be replaced by —O—, —CO—O—, —O—CO—, —CH halogen- or —CHCN—, X and Y are each, independently of one another, F, Cl, Br, CF$_3$, CN, COO-alkyl or alkyl having 1 to 6 carbon atoms one of the radicals X and Y is alternatively H, and m is 0, 1, 2 or 3, with the proviso that, in the case where m=0, A$^2$ is 1,4-phenylene and Z$^2$ is a single bond, and X and Y are not simultaneously F.

The invention furthermore relates to the use of these compounds as components of liquid-crystalline media and to liquid-crystal and electro-optical display elements which contain the liquid-crystalline media according to the invention.

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering.

The invention had an object of finding novel stable liquid-crystalline or mesogenic compounds which are suitable as components of liquid-crystalline media and have, in particular, relatively low viscosity and moderate positive dielectric anisotropy.

It has now been found that compounds of the formula I are eminently suitable as components of liquid-crystalline phases. In particular, they have relatively low viscosities. They can be used to obtain stable liquid-crystalline phases having a broad mesophase range advantageous values for the optical and dielectric anisotropy, which are simultaneously distinguished by very favorable values for the specific resistance. This allows significant advantages to be achieved, in particular in the case of media for active matrix displays or supertwist displays.

Similar compounds containing a disubstituted methylenecyclobutane group are already known. However, these do not have liquid-crystalline properties.

W. R. Dolbier, et al., Tetrahedron Letters 28 (14), 1491–1492, 1987, describe, for example, the preparation of 3-phenyl-1-(difluoromethylene)cyclobutane and 3-phenyl-2,2-difluoro-1-methylenecyclobutane and the cycloaddition of difluoroalkene to styrene.

In addition, the provision of the compounds of the formula I very generally considerably broadens the range of liquid-crystalline substances which are suitable from various applicational points of view for the preparation of liquid-crystalline mixtures.

The compounds of the formula I have a broad range of applications. Depending on the chosen substituents, these compounds can be used as base materials from which liquid-crystalline phases are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

The compounds of the formula I according to the invention containing a chiral group of the formula

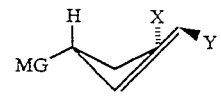

in which X and Y are different from one another, and MG is a mesogenic radical, are particularly suitable as dopants for chiral tilted smectic phases having ferroelectric properties.

In the pure state, the compounds of the formula I are colorless and form liquid-crystalline mesophases in a temperature range which is favorably located for electro-optical use. They are stable chemically, thermally and to light.

The invention thus relates to the compounds of the formula I, in particular the optically active compounds of the formula I in which X and Y are different from one another, and to the compounds of the formula IA

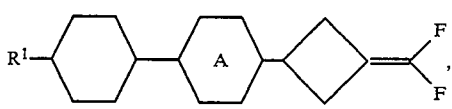

in which
R$^1$ is alkyl having 1 to 15 carbon atoms, and

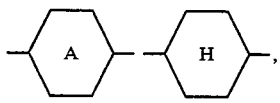

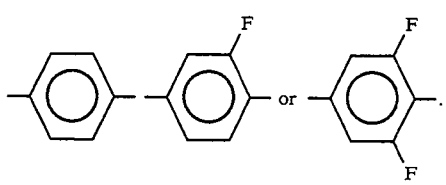

In particular, the invention relates to compounds of the formula I in which at least one of the radicals A$^1$ and A$^2$ is optionally fluorine-substituted 1,4-phenylene, 1,4-cyclohexylene, pyrimidine-2,5-diyl or pyridine-2,5-diyl.

The invention furthermore relates to the use of these compounds as components of liquid-crystalline media. The invention furthermore relates to liquid-crystalline media containing at least one compound which contains a group of the formula

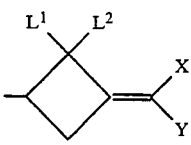

in which L$^1$, L$^2$, X and Y are as defined above, preferably a compound of the formula I, in particular chirally [sic] tilted media containing at least one optically active compound of the formula I. And liquid-crystal display elements, in particular electro-optical display elements, which contain media of this type, in particular matrix liquid-crystal displays.

For reasons of simplicity below, Cbu=—CXY denotes a radical of the formula

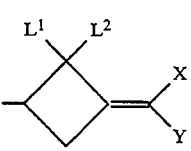

Cyc denotes a 1,4-cyclohexylene radical, Che denotes a 1,4-cyclohexylene radical, Dio denotes a 1,3-dioxane-2,5-diyl radical, Dit denotes a 1,3-dithiane-2,5-diyl radical, Phe denotes a 1,4-phenyl radical, PheF denotes a mono- or di-fluorine-substituted 1,4-phenylene radical, Pyd denotes pyridine-2,5-diyl radical, Pyr denotes a pyrimidine-2,5-diyl radical and Bi denotes a bicyclo-(2,2,2)octylene radical, where Cyc and/or Phe may be unsubstituted or monosubstituted or disubstituted by F or CN.

Accordingly, the compounds of the formula I include bicyclic compounds of the sub-formulae Ia to Ib:

| | |
|---|---|
| R$^1$—A$^2$—Cbu=CXY | Ia |
| R$^1$—A$^2$—Z$^1$—Cbu=CXY | Ib | tricyclic compounds of the sub-formulae Ic to If:

| | |
|---|---|
| R$^1$—A$^1$—A$^2$—Cbu=CXY | Ic |
| R$^1$—A$^1$—Z$^1$—A$^2$—Cbu=CXY | Id |
| R$^1$—A$^1$—A$^2$—Z$^2$—Cbu=CXY | Ie |
| R$^1$—A$^1$—Z$^1$—A$^2$—Z$^2$—Cbu=CXY | If | and tetracyclic compounds of the sub-formulae Ig to In:

| | |
|---|---|
| R$^1$—A$^1$—A$^1$—A$^2$—Cbu=CXY | Ig |
| R$^1$—A$^1$—Z$^1$—A$^1$—A$^2$—Cbu=CXY | Ih |
| R$^1$—A$^1$—A$^1$—Z$^1$—A$^2$—Cbu=CXY | Ii |
| R$^1$—A$^1$—A$^1$—A$^2$—Z$^2$—Cbu=CXY | Ij |
| R$^1$—A$^1$—Z$^1$—A$^1$—Z$^1$—A$^2$—Cbu=CXY | Ik |
| R$^1$—A$^1$—Z$^1$—A$^1$—A$^2$—Z$^2$—Cbu=CXY | Il |
| R$^1$—A$^1$—A$^1$—Z$^1$—A$^2$—Z$^2$—Cbu=CXY | Im |
| R$^1$—A$^1$—Z$^1$—A$^1$—Z$^1$—A$^2$—Z$^2$—Cbu=CXY | In |

Of these, particular preference is given to those of the sub-formulae Ia, Ib, Ic, Id, Ie, If, Ig, Ii and Il.

Preferred compounds of the sub-formula Ia include those of the sub-formulae Iaa to Iah:

| | |
|---|---|
| R$^1$—Phe—Cbu=CXY | Iaa |
| R$^1$—Bi—Cbu—CXY | Iab |
| R$^1$—Dio—Cbu=CXY | Iac |
| R$^1$—Pyr—Cbu=CXY | Iad |
| R$^1$—Pyd—Cbu=CXY | Iae |
| R$^1$—Cyc—Cbu=CXY | Iaf |
| R$^1$—Dit—Cbu=CXY | Iag |
| R$^1$—Che—Cbu=CXY | Iah |

Of these, particular preference is given to those of the formulae Iaa, Iab, Iac, Iad, Iaf and Iag.

The preferred compounds of the sub-formula Ib include those of the sub-formulae Iba to Ibm:

| | |
|---|---|
| R$^1$—Phe—CH$_2$CH$_2$—Cbu=CXY | Iba |
| R$^1$—Phe—OCH$_2$—Cbu—CXY | Ibb |
| R$^1$—Cyc—CH$_2$CH$_2$—Cbu=CXY | Ibc |
| R$^1$—Dio—CH$_2$—CH$_2$—Cbu=CXY | Ibd |
| R$^1$—Phe—COO—Cbu=CXY | Ibe |
| R$^1$—Cyc—COO—Cbu=CXY | Ibf |
| R$^1$—A$^1$—CH$_2$CH$_2$—Cbu=CXY | Ibg |
| R$^1$—A$^1$—C≡C—Cbu=CXY | Ibh |
| R$^1$—A$^1$—CH$_2$O—Cbu=CXY | Ibi |

-continued

| | |
|---|---|
| R$^1$—A$^1$—OCH$_2$—Cbu=CXY | Ibj |
| R$^1$—A$^1$—COO—Cbu=CXY | Ibk |
| R$^1$—A$^1$—OCO—Cbu=CXY | Ibl |
| R$^1$—Che—CH$_2$CH$_2$—Cbu=CXY | Ibm |

The preferred compounds of the sub-formula Ic include those of the sub-formulae Ica to Icm:

| | |
|---|---|
| R$^1$—Phe—Phe—Cbu=CXY | Ica |
| R$^1$—Phe—Pyd—Cbu=CXY | Icb |
| R$^1$—Phe—Dio—Cbu=CXY | Icc |
| R$^1$—Cyc—Cyc—Cbu=CXY | Icd |
| R$^1$—Dio—Cyc—Cbu=CXY | Ice |
| R$^1$—Pyd—Phe—Cbu=CXY | Icf |
| R$^1$—Pyr—Phe—Cbu=CXY | Icg |
| R$^1$—Phe—Pyr—Cbu=CXY | Ich |
| R$^1$—Cyc—Phe—Cbu=CXY | Ici |
| R$^1$—Dit—Phe—Cbu=CXY | Icj |
| R$^1$—Dio—Phe—Cbu=CXY | Ick |
| R$^1$—Che—Phe—Cbu=CXY | Icl |
| R$^1$—Phe—Che—Cbu=CXY | Icm |

Of these, particular preference is given to those of the formulae Ica, Icc, Icd, Ice, Ici and Icj.

The preferred compounds of the sub-formula Id include those of the sub-formulae Ida to Idm:

| | |
|---|---|
| R$^1$—Phe—Z$^1$—Phe—Z$^1$—Cbu=CXY | Ida |
| R$^1$—Phe—Z$^1$—Bi—Z$^1$—Cbu=CXY | Idb |
| R$^1$—Phe—Z$^1$—Dio—Z$^1$—Cbu=CXY | Idc |
| R$^1$—Cyc—Z$^1$—Cyc—Z$^1$—Cbu=CXY | Idd |
| R$^1$—Dio—Z$^1$—Cyc—Z$^1$—Cbu=CXY | Ide |
| R$^1$—Pyd—Z$^1$—Phe—Z$^1$—Cbu=CXY | Idf |
| R$^1$—Phe—Z$^1$—Pyd—Z$^1$—Cbu=CXY | Idg |
| R$^1$—Pyr—Z$^1$—Phe—Z$^1$—Cbu=CXY | Idh |
| R$^1$—Phe—Z$^1$—Pyr—Z$^1$—Cbu=CXY | Idi |
| R$^1$—Phe—Z$^1$—Cyc—Z$^1$—Cbu=CXY | Idj |
| R$^1$—Cyc—Z$^1$—Phe—Z$^1$—Cbu=CXY | Idk |
| R$^1$—Dio—Z$^1$—Phe—Z$^1$—Cbu=CXY | Idl |
| R$^1$—Che—Z$^1$—Phe—Z$^1$—Cbu=CXY | Idm |

The preferred compounds of the sub-formula Ie include those of the sub-formulae Iea to Iek:

| | |
|---|---|
| R$^1$—Pyr—Z$^1$—Phe—Cbu=CXY | Iea |
| R$^1$—Dio—Z$^1$—Phe—Cbu=CXY | Ieb |
| R$^1$—Cyc—Z$^1$—Phe—Cbu=CXY | Iec |
| R$^1$—Cyc—Z$^1$—Dio—Cbu=CXY | Ied |
| R$^1$—Phe—Z$^1$—Cyc—Cbu=CXY | Iee |
| R$^1$—Dio—Z$^1$—Cyc—Cbu=CXY | Ief |
| R$^1$—Cyc—Z$^1$—Cyc—Cbu=CXY | Ieg |
| R$^1$—Phe—Z$^1$—Dio—Cbu=CXY | Ieh |
| R$^1$—Pyd—Z$^1$—Phe—Cbu=CXY | Iei |
| R$^1$—Phe—Z$^1$—Pyr—Cbu=CXY | Iej |
| R$^1$—Phe—Z$^1$—Che—Cbu=CXY | Iek |

The preferred compounds of the sub-formula If include those of the sub-formulae Ifa to Ifp

| | |
|---|---|
| R$^1$—Pyr—Phe—Z$^1$—Cbu=CXY | Ifa |
| R$^1$—Pyr—Phe—OCH$_2$—Cbu=CXY | Ifb |
| R$^1$—Bi—Phe—Z$^1$—Cbu=CXY | Ifc |
| R$^1$—Phe—Phe—Z$^1$—Cbu=CXY | Ifd |
| R$^1$—Pyr—Cyc—Z$^1$—Cbu=CXY | Ife |
| R$^1$—Cyc—Cyc—Z$^1$—Cbu=CXY | Iff |
| R$^1$—Cyc—Cyc—CH$_2$CH$_2$—Cbu=CXY | Ifg |
| R$^1$—Pyd—Phe—Z$^1$—Cbu=CXY | Ifh |
| R$^1$—Dio—Phe—Z$^1$—Cbu=CXY | Ifi |
| R$^1$—Dio—Cyc—Z$^1$—Cbu=CXY | Ifj |
| R$^1$—Phe—Cyc—Z$^1$—Cbu=CXY | Ifk |
| R$^1$—Phe—Pyd—Z$^1$—Cbu=CXY | Ifl |
| R$^1$—Che—Phe—Z$^1$—Cbu=CXY | Ifm |
| R$^1$—Phe—Che—Z$^1$—Cbu=CXY | Ifn |
| R$^1$—Cyc—Phe—Z$^1$—Cbu=CXY | Ifo |
| R$^1$—Cyc—Dio—Z$^1$—Cbu=CXY | Ifp |

The preferred compounds of the formulae [sic] Ig include those of the formulae Iga to Igf:

| | |
|---|---|
| R$^1$—Phe—Phe—Phe—Cbu=CXY | Iga |
| R$^1$—Cyc—Phe—Phe—Cbu=CXY | Igb |
| R$^1$—Cyc—Cyc—Phe—Cbu=CXY | Igc |
| R$^1$—Phe—Cyc—Cyc—Cbu=CXY | Igd |
| R$^1$—Cyc—Cyc—Cyc—Cbu=CXY | Ige |
| R$^1$—Cyc—Phe—Phe—Cbu=CXY | Igf |

In the compounds of the formulae above and below, the radicals X and Y are preferably different from one another.

The terminal group Cbu=CXY is thus preferably a group of the formulae 1 to 8:

| | |
|---|---|
| Cbu=CHF | 1 |
| Cbu=CHCl | 2 |
| Cbu=CHCF$_3$ | 3 |

| | |
|---|---|
| Cbu=CFCl | 4 |
| Cbu=CF—CF$_3$ | 5 |
| Cbu=CCl—CF$_3$ | 6 |
| Cbu=CF$_2$ | 7 |
| Cbu=CCl$_2$ | 8 |

$R^1$ is preferably alkyl, furthermore alkoxy. $A^1$ or $A^2$ are [sic] preferably Phe, Cyc, Che, Pyr or Dio. The compounds of the formula I preferably contain not more than one of the radicals Bi, Pyd, Pyr, Dio or Dit.

Preference is also given to compounds of the formula I and of all sub-formulae in which $A^1$ and/or $A^2$ is 1,4-phenylene which is monosubstituted or disubstituted by F or monosubstituted by CN. In particular, these are 2-fluoro-1,4-phenylene, 3-fluoro-1,4-phenylene and 2,3-difluoro-1,4-phenylene, 2,6-difluoro-1,4-phenylene, 3,5-difluoro-1,4-phenylene, and 2-cyano-1,4-phenylene and 3-cyano-1,4-phenylene.

Particular preference is given to the compounds of the formula I, in which $A^2$ is 1,4-phenylene which is unsubstituted or monosubstituted or disubstituted by F.

$Z^1$ and $Z^2$ are preferably a single bond, —CO—O—, —O—CO— and —CH$_2$CH$_2$, secondarily preferably —CH$_2$O— and —OCH$_2$—.

If $R^1$ is an alkyl radical or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkenyl radical, this may be straight-chain or branched. It is preferably straight-chain and has 2 to 10 carbon atoms. Accordingly, it is in particular vinyl, prop-1-, or prop-2-enyl, but-1-,2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, or dec-1-, 2-, 3-, 4-, 5-, 6-, 7-, 8- or dec -9-enyl.

If $R^1$ is an alkyl radical in which one CH$_2$ group has been replaced by —O— and one has replaced by —CO—, these are preferably adjacent. These thus contain an acyloxy group —CO—O— or an oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl) ethyl, 2-(ethoxacarbonyl)ethyl [sic], 2-(propoxycarbonyl)ethyl, 3 -(methoxycarbonyl)propyl, 3-(ethoxycarbonyl)propyl or 4-(methoxycarbonyl)butyl.

If $R^1$ is an alkenyl radical in which one CH$_2$ group has been replaced by CO or CO—O or O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

Compounds of the formula I which contain wing groups $R^1$ which are suitable for polymerization reactions are suitable for the preparation of liquid-crystalline polymers.

Compounds of the formulae [sic] I containing branched wing groups $R^1$ may occasionally be of importance due to better solubility in the conventional liquid-crystalline base materials, but in particular as chiral dopes if they are optically active. Smectic compounds of this type are suitable as components of ferroelectric materials. Compounds of the formula I having $S_A$ phases are suitable, for example, for thermally addressed displays.

Branched groups of this type generally contain not more than one chain branch. Preferred branched radicals $R^1$ are isopropyl, 2 -butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy [sic], 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Preferred optically active compounds of the formula I contain, as chiral radical, a group of the formula

in which X and Y are different from one another.

If $R^1$ is an alkyl radical in which two or more CH$_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)-propyl, 4,4-bis(ethoxycarbonyl)butyl or 5,5-bis(ethoxycarbonyl)hexyl.

Compounds of the formula I which contain wing groups $R^1$ which are suitable for polycondensation reactions are suitable for the preparation of liquid-crystalline polycondensates.

Formula I covers the racemates of these compounds and the optical antipodes, and mixtures thereof.

$R^1$ is preferably F, Cl, $CF_3$, $OCF_3$ or $OCF_2H$, in particular if X and Y are H or alkyl. $L^1$ and $L^2$ are preferably identical and are F, Cl or H, in particular H.

Of these compounds of the formula I and the sub-formulae, preference is given to those in which at least one of the radicals present therein has one of the preferred meanings indicated.

In the compounds of the formula I, preferred stereoisomers are those in which the rings Cyc and piperidine are trans-1,4-disubstituted. Those of the abovementioned formulae which contain one or more groups Pyd, Pyr, Dit and/or Dio in each case cover both of the 2,5-positional isomers.

Particularly preferred compounds of the formula I which contain a group of the formula 1 are those of the sub-formulae I1a to I1n:

| | |
|---|---|
| alkyl-Cyc—Cbu=CHF | I1a |
| alkyl-Phe—Cbu=CHF | I1b |
| alkyl-Cyc—Cyc—Cbu=CHR | I1c |
| alkyl-Cyc—Phe—Cbu=CHF | I1d |
| alkyl-Cyc—CH₂CH₂—Cbu—CHF | I1e |
| alkyl-Phe—CH₂CH₂—Cbu=CHF | I1f |
| alkyl-Phe—CO—O—Cbu=CHF | I1g |
| alkyl-Cyc—CO—O—Cbu=CHF | I1h |
| alkyl-Cyc—Phe—C≡C—Cbu=CHF | I1i |
| alkyl-Cyc—Phe—CH₂CH₂—Cbu=CHF | I1j |
| alkyl-Cyc—Cyc—CH₂CH₂—Cbu=CHF | I1k |
| alkyl-Phe—Phe—CH₂CH₂—Cbu=CHF | I1l |
| alkyl-Cyc—CH₂CH₂—Cyc—Cbu=CHF | I1m |
| alkyl-Cyc—PheF—Cbu=CHF | I1n |

Particularly preferred compounds of the formula I which contain a group of the formula 2 are those of the sub-formulae I2a to I2o:

| | |
|---|---|
| alkyl-Phe—Cbu=CHCl | I2a |
| alkyl-Cyc—Cbu=CHCl | I2b |
| alkyl-Cyc—Phe—Cbu=CHCl | I2c |
| alkyl-Cyc—Cyc—Cbu=CHCl | I2d |
| alkyl-Phe—Phe—Cbu=CHCl | I2e |
| alkyl-Phe—CH₂CH₂—Cbu=CHCl | I2f |
| alkyl-Cyc—CH₂CH₂—Cbu=CHCl | I2g |
| alkyl-Cyc—CO—O—Cbu=CHCl | I2h |
| alkyl-Phe—CO—O—Cbu=CHCl | I2i |
| alkyl-Cyc—Phe—C≡C—Cbu=CHCl | I2j |
| alkyl-Cyc—Phe—CH₂CH₂—Cbu—CHCl | I2k |
| alkyl-Cyc—Cyc—CH₂CH₂—Cbu=CHCl | I2l |
| alkyl-Phe—Phe—CH₂CH₂—Cbu=CHCl | I2m |
| alkyl-Cyc—CH₂CH₂—Cyc—Cbu=CHCl | I2n |
| alkyl-Cyc—PheF—Cbu=CHCl | I2o |

Particularly preferred compounds of the formula I which contain a group of the formula 7 are those of the sub-formulae I7a to I7o:

| | |
|---|---|
| alkyl-PheF—Cbu=CF₂ | I7a |
| alkyl-Cyc—Cbu=CF₂ | I7b |
| alkyl-Cyc—Phe—Cbu=CF₂ | I7c |
| alkyl-Cyc—Cyc—Cbu=CF₂ | I7d |
| alkyl-Phe—Phe—Cbu=CF₂ | I7e |
| alkyl-Phe—CH₂CH₂—Cbu=CF₂ | I7f |
| alkyl-Cyc—CH₂CH₂—Cbu=CF₂ | I7g |
| alkyl-Cyc—CO—O—Cbu=CF₂ | I7h |
| alkyl-Phe—CO—O—Cbu=CF₂ | I7i |
| alkyl-Cyc—Phe—C≡C—Cbu—CF₂ | I7j |
| alkyl-Cyc—Phe—CH₂CH₂—Cbu=CF₂ | I7k |
| alkyl-Cyc—Cyc—CH₂CH₂—Cbu=CF₂ | I7l |
| alkyl-Phe—Phe—CH₂CH₂—Cbu=CF₂ | I7m |
| alkyl-Cyc—CH₂CH₂—Cyc—Cbu=CF₂ | I7n |
| alkyl—Cyc—PheF—Cbu=CF₂ | I7o |

Particularly preferred compounds of the formula I which contain a group of the formula 8 are those of the formulae I8a to I8o:

| | |
|---|---|
| alkyl-Phe—Cbu=CCl₂ | I8a |
| alkyl-Cyc—Cbu=CCl₂ | I8b |
| alkyl-Cyc—Phe—Cbu=CCl₂ | I8c |
| alkyl-Cyc—Cyc—Cbu=CCl₂ | I8d |
| alkyl-Phe—Phe—Cbu=CCl₂ | I8e |
| alkyl-Phe—CH₂CH₂—Cbu=CCl₂ | I8f |
| alkyl-Cyc—CH₂CH₂—Cbu=CCl₂ | I8g |
| alkyl-Cyc—CO—O—Cbu=CCl₂ | I8h |
| alkyl-Phe—CO—O—Cbu=CCl₂ | I8i |
| alkyl-Cyc—Phe—C≡C—Cbu=CCl₂ | I8j |
| alkyl-Cyc—Phe—CH₂CH₂—Cbu=CCl₂ | I8k |
| alkyl-Cyc—Cyc—CH₂CH₂—Cbu=CCl₂ | I8l |
| alkyl-Phe—Phe—CH₂CH₂—Cbu=CCl₂ | I8m |
| alkyl-Cyc—CH₂CH₂—Cyc—Cbu—CCl₂ | I8n |

-continued

In the above compounds of the sub-formulae IIa to IIm, I2a to I2n, I7a to I7n and I8a to I8n, alkyl- in each case denotes alkyl or alkoxy groups having 1 to 12 carbon atoms.

The 1,4-cyclohexenylene group preferably has the following structures:

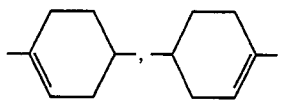

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart, to be precise under reaction conditions which are known and suitable for said reactions. Use may also be made here of variants which are known per se, but are not -continued

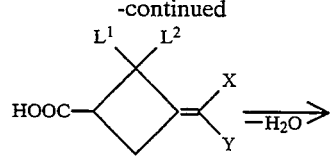

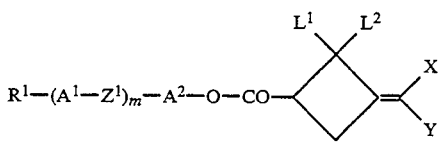

The methylenecyclobutanecarboxylic acid derivatives can be prepared from the corresponding nitriles by means of aqueous sodium hydroxide solution (for example Gripps et al., Am. Soc. 81 (1959), 2723-2728).

The compounds of the formula I can furthermore be prepared from the corresponding 3-substituted cyclobutanones by condensation with methane derivatives by the method of C. Burton et al., Tetrahedron Lett. 29 (24), 3003-6 (1988) or J. Fried, et al., Tetrahedron Lett. 25, 4329 (1984) in the presence of a phosphine (for example Scheme 3)

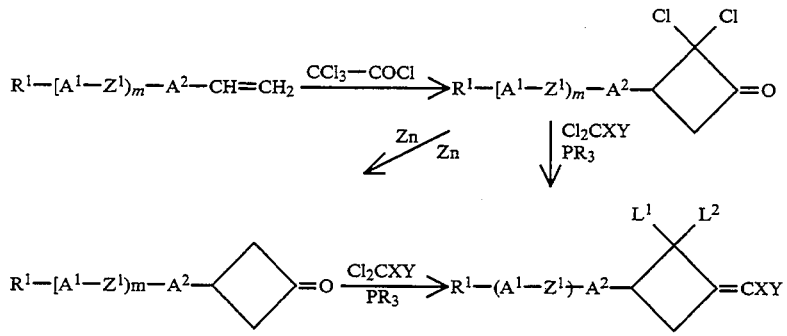

described here in greater detail.

The compounds of the formula I can be prepared, for example, analogously to the processes described by Dobier et al. (J. Am. Chem. Soc. 107 (12), 3626-31 (1985)) by cycloaddition of alkenes onto styrene derivatives (cf. Scheme I):

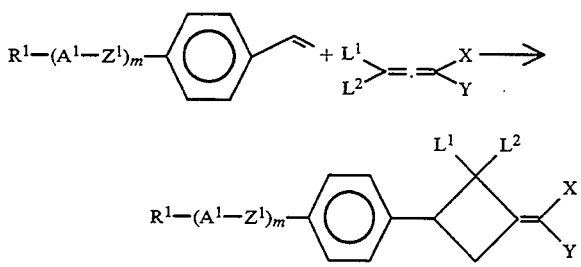

The compounds of the formula I in which $Z^2$ is —O—CO— can be obtained be esterification of 3-methylenecyclobutanoic acid in accordance with Scheme 2

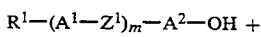

Furthermore, the compounds of the formula I can be prepared by reducing a compound which contains one or more reducible groups and/or C—C bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction conform to the formula I, but contain a cyclohexene ring or cyclohexanone ring in place of a cyclohexane ring and/or contain a —CH=CH— group in place of a —CH$_2$—CH$_2$— group and/or contain a —CO— group in place of a —CH$_2$— group and-/or contain a free or functionally derived (for example in the form of its p-toluenesulfonate) OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are expediently noble metals, such as Pt or Pd, which may be employed in the form of oxides (for example PtO$_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, expediently in aqueous-alcoholic solution or in the heterogeneous phase with water/toluene at temperatures between about 80° and 120°) or Wolff-Kishner (using hydrazine, expediently in the presence of alkali, such as KOH or NaOH, in a high-boiling solvent, such as diethylene glycol or triethylene glycol, at temperatures between about 100° and 200°) to give the corresponding compounds of the formula I which contain alkyl groups and/or —$CH_2CH_2$— bridges.

Furthermore, reductions using complex hydrides are possible. For example, arylsulfonyloxy groups can be removed reductively using $LiAlH_4$, in particular p-toluenesulfonyloxymethyl groups can be reduced to methyl groups, expediently in an inert solvent such as diethyl ether or THF, at temperatures between about 0° and 100°. Double bonds can be hydrogenated using $NaBH_4$ or tributyltin hydride in methanol.

Compounds of the formula I which conform to the formula I but contain 1,4-cyclohexylene radicals in place of 1,4-phenylene radicals can be oxidized, for example, by means of DDQ (dichlorodicyanobenzoquinone) in a suitable solvent.

Esters of the formula I can also be obtained by esterification of corresponding carboxylic acids (or reactive derivatives thereof), in particular of the formula IV, by means of alcohols or phenols (or reactive derivatives thereof), in particular of the formula V, or by the DCC method (DCC=dicyclohexylcarbodiimide).

The corresponding carboxylic acids and alcohols or phenols are known and can be prepared analogously to known processes.

Particularly suitable reactive derivatives of the said carboxylic acids are the acyl halides, in particular the chlorides and bromides, furthermore the anhydrides, for example also mixed anhydrides, azides or esters, in particular alkyl esters having 1–4 carbon atoms in the alkyl group.

Particularly suitable reactive derivatives of said alcohols or phenols are the corresponding metal alkoxides or phenoxides, preferably of an alkali metal such as sodium or potassium.

The esterification is advantageously carried out in the presence of an inert solvent. Particularly suitable solvents are ethers, such as, for example, diethyl ether, di-n-butyl ether, THF, dioxane or anisole, ketones, such as, for example, acetone, butanone or cyclohexanone, amides, such as, for example, DMF or hexamethylphosphoric triamide, hydrocarbons, such as, for example, benzene, toluene or xylene, halogenated hydrocarbons, such as, for example, tetrachloromethane, dichloromethane or tetrachloroethylene, and sulfoxides, such as, for example, dimethyl sulfoxide or sulfolane.

In order to prepare nitriles of the formula I, corresponding acid amides, for example those in which a $CONH_2$ group replaces the CN radical, can be dehydrated. The amides are obtainable, for example, from corresponding esters or acyl halides by reaction with ammonia. Examples of suitable dehydrating agents are inorganic acid chlorides, such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as a double compound with NaCl), aromatic sulfonic acids and sulfonic acid halides. The reaction can be carried out here in the presence or absence of an inert solvent at temperatures between about 0° C.

and 150°; examples of suitable solvents are bases, such as pyridine or triethylamine, aromatic hydrocarbons, such as benzene, toluene or xylene, or amides, such as DMF.

The abovementioned nitriles of the formula I can also be prepared by reacting corresponding acyl halides, preferably the chlorides, with sulfamide, expediently in an inert solvent, such as tetramethylene sulfone, at temperatures between about 80° and 150°, preferably at 120°. After customary work-up, the nitriles can be isolated directly.

Ethers of the formula I can be obtained by etherification of corresponding hydroxyl compounds, in particular of the formula VI or VII, preferably the corresponding phenols, the hydroxyl compound expediently first being converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, alkyl sulfonate or dialkyl sulfate, expediently in an inert solvent, such as, for example, acetone, 1,2-dimethoxyethane, DMF or dimethyl sulfoxide, or alternatively an excess of aqueous or aqueous-alcoholic NaOH or KOH at temperatures between about 20° and 100°.

Nitriles of the formula I can also be prepared by reacting corresponding chlorine, bromine or iodine compounds of the formula I with a cyanide, preferably with a metal cyanide, such as, for example, NaCN, KCN or $Cu_2(CN)_2$, for example in the presence of pyridine in an inert solvent, such as, for example, DMF or N-methylpyrrolidone, at temperatures between 20° and 200°.

Compounds of the formula I in which $A^1$ is substituted by at least one F atom and/or CN group can also be obtained from the corresponding diazonium salts by replacement of the diazonium group by a fluorine atom or by a CN group, for example by the methods of Schiemann or Sandmeyer.

Dioxane derivatives and dithiane derivatives of the formula I are expediently prepared by reacting an appropriate aldehyde (or a reactive derivative thereof) with an appropriate 1,3-diol (or a reactive derivative thereof) or an appropriate 1,3-dithiol, preferably in the presence of an inert solvent, such as, for example, benzene or toluene, and/or in the presence of a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known and some can be prepared without difficulty from compounds known from the literature by standard methods of organic chemistry. For example, the aldehydes can be obtained by oxidation of corresponding alcohols or by reduction of nitriles or corresponding carboxylic acids or derivatives thereof, the diols can be obtained by reduction of corresponding diesters, and the dithiols by reaction of corresponding dihalides with NaSH.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylidenanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

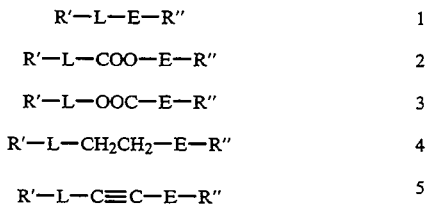

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, —OCHF$_2$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

EXAMPLES

The examples below are intended to illustrate the invention without representing a limitation. m.p. =melting point, c.p. =clearing point. Above and below, percentages are percent by weight; all temperatures are indicated in degrees Celsius. "Customary work-up" means that water is added, the mixture is extracted with methylene chloride, and the organic phase is separated off, dried and evaporated, and the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

| | |
|---|---|
| DAST | diethylaminosulfur trifluoride |
| DCC | dicyclohexylcarbodiimide |
| DDQ | dichlorodicyanobenzoquinone |
| DIBALH | diisobutylaluminum hydride |
| HMTAP | hexamethyltriaminophosphine |
| POT | potassium tertiary-butanolate |
| PCC | pyridinium chlorochromate |
| THF | tetrahydrofuran |
| TPP | triphenylphosphine |
| pTSOH | p-toluenesulfonic acid |

Example 1

Preparation of 3-[4-(trans-4-pentylcyclohexyl)phenyl]-1-(difluoromethylene)cyclobutane A) 4-(trans-4-pentylcyclohexyl)vinylbenzene 1 mol of BuLi is added at −70° C. to a mixture of 1 mol of 4-(trans-pentylcyclohexyl)bromobenzene and 3 l of THF. A mixture of 0.5 mol of zinc bromide in 1 l of THF is subsequently added, and the reaction mixture is stirred at −65° C. for 30 minutes. 1 mol of vinyl bromide and 0.022 mol of nickel(II) chloride/TPP are subsequently added.

The reaction mixture is stirred at room temperature for 16 hours and subjected to customary work-up. The styrene derivative obtained is processed further without purification.

B) 3-[4-(trans-4-pentylcyclohexyl)phenyl]-2,2-dichlorocyclobutanone 0.25 mol of trichloroacetyl chloride is added over the course of 15 minutes to a mixture of 0.25 mol of 1A, 23.0 g of zinc/copper (3% of copper) and 800 ml of diethyl ether, and the mixture is subsequently stirred under reflux for 8 hours. Customary work-up gives the product, which is processed further without purification.

C) 3-[4-(trans-4-pentylcyclohexyl)phenyl]cyclobutanone

A mixture of 0.144 mol of 1B, 0.53 mol of zinc powder and 880 ml of glacial acetic acid is stirred at room temperature for 17 hours. Conventional work-up gives the product, which is processed further without purification.

D)

A mixture of 0.3 mol of hexamethyltriaminophosphine and 50 ml of tetraglyme is added at 0° C. to a mixture of 1.5 mol of dibromidefluoromethane [sic], 100 ml of tetraglyme. 0.075 and [sic] 1C are subsequently added, and the mixture is stirred at room temperature for 16 hours. Customary work-up and crystallization from 100 ml of ethanol/ethyl acetate give the pure product, C 42 I, $\Delta\epsilon +2.85$, $\Delta n$ 0.071.

The following are prepared analogously

3-[4-(trans-4-propylcyclohexyl)phenyl]-1-(difluoromethylene)cyclobutane

3-[4-(trans-4-ethylcyclohexyl)phenyl]-1-(difluoromethylene)cyclobutane

3-[4-(trans-4-butylcyclohexyl)phenyl]-1-(difluoromethylene)cyclobutane

3-[4-(trans-4-hexylcyclohexyl)phenyl]-1-(difluoromethylene)cyclobutane

3-[4-(trans-4-heptylcyclohexyl)phenyl]-1-(difluoromethylene)cyclobutane

3-[4-[trans-4-ethylcyclohexyl)-2,3-difluorophenyl]-1-(difluoromethylene)cyclobutane 3-[4-[trans-4-propylcyclohexyl)-2,3-difluorophenyl]-1-(difluoromethylene)cyclobutane 3-[4-[trans-4-pentylcyclohexyl)-2,3-difluorophenyl]-1-(difluoromethylene)cyclobutane 3-[4-[trans-4-hexylcyclohexyl)-2,3-difluorophenyl]-1-(difluoromethylene)cyclobutane 3-[4-[trans-4-heptylcyclohexyl)-2,3-difluorophenyl]-1-(difluoromethylene)cyclobutane 3-[4-[trans-4-ethylcyclohexyl)-2,6-difluorophenyl]-1-(difluoromethylene)cyclobutane 3-[4-[trans-4-propylcyclohexyl)-2,6-difluorophenyl]-1-(difluoromethylene)cyclobutane 3-[4-[trans-4-pentylcyclohexyl)-2,6-difluorophenyl]-(difluoromethylene)cyclobutane, C 29 I 3-[4-[trans-4-hexylcyclohexyl)-2,6-difluorophenyl]-1-(difluoromethylene)cyclobutane 3-[4-[trans-4-heptylcyclohexyl) -2,6-difluorophenyl]-1-(difluoromethylene)cyclobutane 3-(trans-4-ethylcyclohexyl)-1-(difluoromethylene)cyclobutane 3-(trans-4-propylcyclohexyl)-1-(difluoromethylene)cyclobutane 3-(trans-4-butylcyclohexyl)-1-(difluoromethylene)cyclobutane 3-(trans-4-pentylcyclohexyl)-1-(difluoromethylene)cyclobutane 3-(trans-4-hexylcyclohexyl)-1-(difluoromethylene)cyclobutane 3-(trans-4-heptylcyclohexyl)-1-(difluoromethylene)cyclobutane 3-(trans-4-octylcyclohexyl)-1-(difluoromethylene)cyclobutane 3-[trans,trans-4-(4-ethylcyclohexyl)cyclohexyl]-1-(difluoromethylene)cyclobutane, $\Delta n$ 0.073, $\Delta\epsilon = 4.20$ 3-[trans,trans-4-(4-propylcyclohexyl)cyclohexyl]-1-(difluoromethylene)cyclobutane, $\Delta n$ 0.058, $\Delta\epsilon = 2.97$ 3-[trans,trans-4-(4-butylcyclohexyl)cyclohexyl]-1-(difluoromethylene)cyclobutane, C 40 $S_B$ 99 N 104 I, $\Delta\epsilon = 3.03$, $\Delta n = 0.067$ 3-[trans,trans-4-(4-pentylcyclohexyl)cyclohexyl]-1-(difluoromethylene)cyclobutane, C 38 $S_B$ 99 N 112.1 I, $\Delta\epsilon = 4.18$, $\Delta n = 0.072$ 3-[trans, trans-4-(4-hexylcyclohexyl)cyclohexyl]-1-(difluoromethylene)cyclobutane 3-[trans, trans-4-(4-heptylcyclohexyl)cyclohexyl]-1-(difluoromethylene)cyclobutane 3-[4-(trans-4-ethylcyclohexyl)-2-fluorophenyl]-1-(difluoromethylene)cyclobutane 3-[4-(trans-4-propylcyclohexyl)-2-fluorophenyl]-1-(difluoromethylene)cyclobutane 3-[4-(trans-4-butylcyclohexyl)-2-fluorophenyl]-1-(difluoromethylene)cyclobutane 3-[4-(trans-4-pentylcyclohexyl)-2-fluorophenyl]-1-(difluoromethylene)cyclobutane 3-[4-(trans-4-hexylcyclohexyl)-2-fluorophenyl]-1-(difluoromethylene)cyclobutane 3-[4-(trans-4-heptylcyclohexyl)-2-fluorophenyl]-1-(difluoromethylene)cyclobutane

Example 2

Preparation of 4-[trans-4-propylcyclohexyl)phenyl 3-isopropylidenecyclobutanecarboxylate A mixture of 0.11 mol of DCC add 50 ml of dichloromethane is added at 0° C. to a mixture of 0.1 mol of 3-isopropylidenecyclobutanecarboxylate [sic] (prepared by the method of Gripps et al., Am. Soc. 81 (1959), 2723–2728) 0.1 mol of 4-(trans-4-propylcyclohexyl)phenol and 100 ml of dichloromethane. After the mixture has been stirred at room temperature for 16 hours and the solid constituents have been removed, conventional work-up gives the product.

The following are prepared analogously:

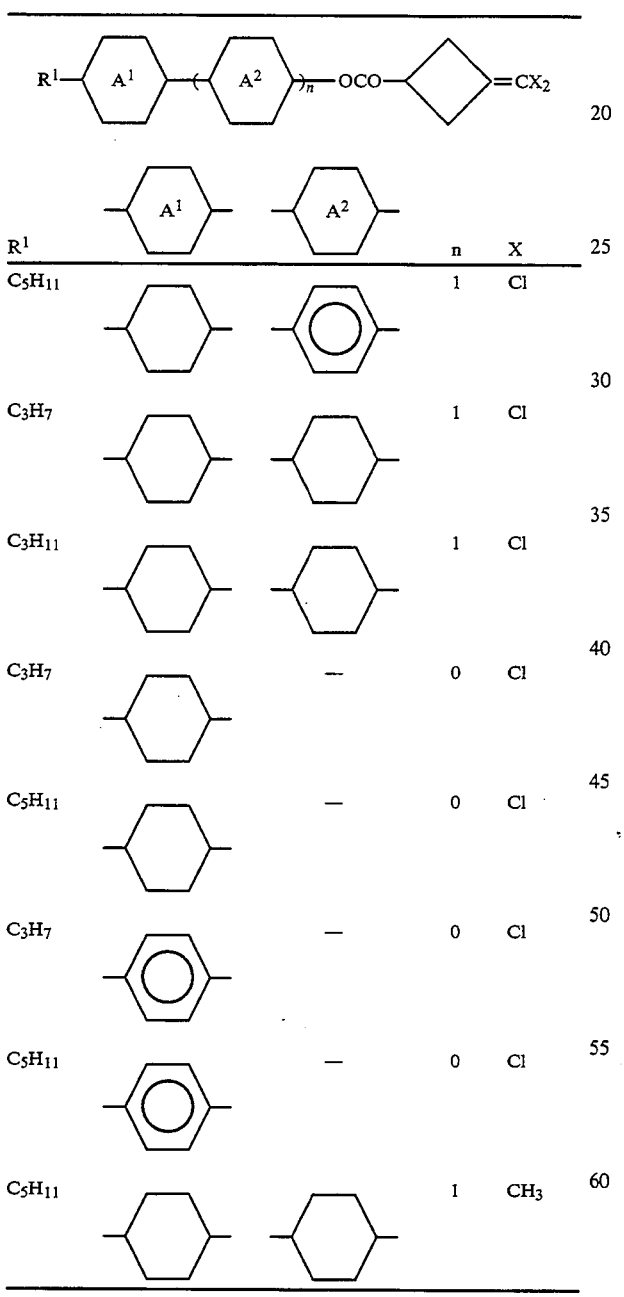

Example 3

A neutral base mixture (B) comprising

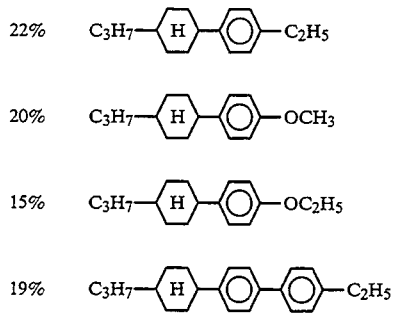

is in each case treated with:

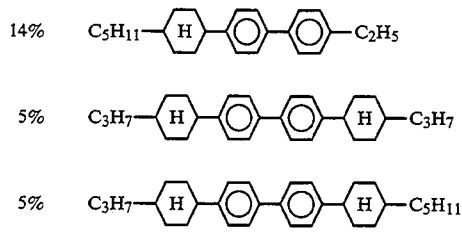

The resultant mixtures are introduced into a test cell.

The voltage holding ratio of these cells is measured at room temperature HR (RT) and after heating to 100° C. HR (100).

| Mixture | HR (RT) | HR (100) |
| --- | --- | --- |
| B | 99.0 | 98.4 |
| B + (1) | 98.2 | 94.2 |
| B + (2) | 98.2 | 97.0 |
| B + (3) | 98.0 | 94.3 |

The measurement of the holding ratio is carried out by the method of G. Weber et al. Liquid Crystals 5, 1320 (1989).

Compounds (1), (2) and (3) are thus suitable for the preparation of mixtures of positive dielectric anisotropy and high values of the holding ratio, in particular for active-matrix displays.

We claim:

1. A methylenecyclobutane derivative of formula I

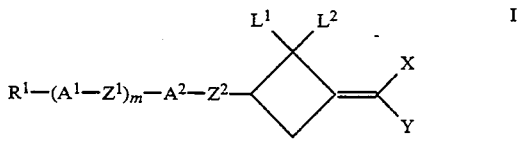

in which
R[1] is halogen, CN, CF$_3$, —OCF$_3$, —OCF$_2$H, or an alkyl, alkenyl or perfluoroalkyl radical having up to 15 carbon atoms which is unsubstituted or monosubstituted by CN, halogen or CF$_3$, wherein one or more CH$_2$ groups in said radical may each, independently of one another, be replaced by —S—,

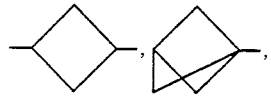

—O—, —CO—, —CO—O—, —O—CO— or —O—CO—O— in such a way that S and/or O atoms are not linked directly to one another, A[1] and A[2] are each, independently of one another, a
(a) trans-1,4-cyclohexylene radical in which, in addition, one or more non-adjacent CH$_2$ groups may be replaced by —O— and/or —S—,
(b) 1,4-phenylene radical in which, in addition, one or two CH groups may be replaced by N,
(c) 1,3-cyclobutylene, 1,3-bicyclo(1,1,1)-pentylene, 1,4-cyclohexenylene, 1,4-bicyclo(2,2,2)-octylene, piperidine-1,4-diyl, naphthalene-2,6-diyl, decahydronaphthalene-2,6-diyl, decahydronaphthalene-2,6-diyl and 1,2,3,4-tetrahydronaphthalene-2,6-diyl radical, wherein the radicals (a) and (b) may be monosubstituted or polysubstituted by CN or halogen, L[1] and L[2] are each H, F or Cl, Z[1] and Z[2] are each, independently of one another —CH$_2$CH$_2$—, —C≡C—, —CH$_2$O—, —OCH$_2$—, —CO—O—, —O—CO—, —CH=N—, —N=CH—, —CH$_2$S—, —SCH$_2$—, a single bond or an alkylene group having 3 to 6 carbon atoms in which, in addition, one CH$_2$ group may be replaced by —O—, —CO—O—, —O—CO—, —CH halogen- or —CHCN—, X and Y are each independently of one another, F, Cl, Br, CF$_3$, CN, COO-alkyl or alkyl having 1 to 6 carbon atoms, one of the radicals X and Y is alternatively H, and m is 0, 1, 2 or 3,
with the proviso that, in the case where m=0, A[2] is 1,4-phenylene and Z[2] is a single bond, and X and Y are not simultaneously F.

2. A derivative of formula I according to claim 1, in which at least one of the radicals A[1] and A[2] is optionally fluorine-substituted 1,4-phenylene, 1,4-cyclohexylene, pyrimidine-2,5-diyl or pyridine-2,5-diyl.

3. A derivative according to claim 1 of formula IA

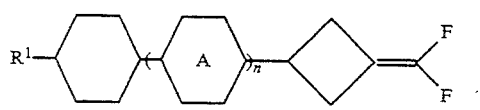

in which
R[1] is alkyl having 1 to 15 carbon atoms

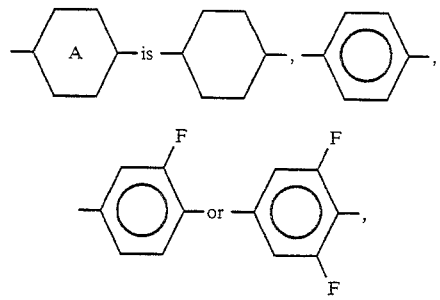

and
n is 0 or 1.

4. A derivative of formula I, according to claim 1, wherein X and Y are different from one another, said derivative being an optically active methylenecyclobutane.

5. A liquid-crystalline medium comprising at least two liquid-crystalline components, wherein at least one component contains a group of the formula

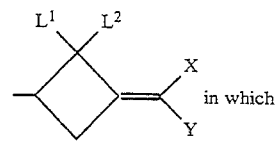

L[1] and L[2] are each H, F or Cl,

X and Y are each independently of one another, F, Cl, Br, CF$_3$, CN, COO-alkyl or alkyl having 1 to 6 carbon atoms, or one of the radicals X and Y is alternatively H.

6. A liquid-crystalline medium comprising at least 2 liquid-crystalline components, wherein at least one component is a compound of formula I according to claim 1.

7. A Chiral tilted liquid-crystalline medium having at least one achiral component and at least one chiral component, wherein at least one chiral component is an optically active methylenecyclobutane derivative of formula I according to claim 4.

8. An electrooptical display, comprising a liquid-crystalline dielectric, which is a liquid-crystalline medium according to claim 5.

9. A matrix liquid-crystal display comprising a liquid-crystalline dielectric, which is a liquid-crystalline medium according to claim 5.

10. An electrooptical display, comprising a liquid-crystalline dielectric, which is a liquid-crystalline medium according to claim 6.

11. A matrix liquid-crystal display comprising a liquid-crystalline dielectric, which is a liquid-crystalline medium according to claim 6.

12. An electrooptical display, comprising a liquid-crystalline dielectric, which is a liquid-crystalline medium according to claim 7.

13. A matrix liquid-crystal display comprising a liquid-crystalline dielectric, which is a liquid-crystalline medium according to claim 7.

* * * * *